(12) United States Patent
Noguchi et al.

(10) Patent No.: US 7,764,360 B2
(45) Date of Patent: Jul. 27, 2010

(54) FUEL PROPERTY DETECTOR

(75) Inventors: Hitoshi Noguchi, Nishio (JP); Rie Osaki, Anjo (JP); Hiroshi Nakamura, Nishio (JP); Hitoshi Uda, Toyota (JP); Yukihiro Tsukasaki, Susono (JP); Hiroki Ichinose, Fujinomiya (JP)

(73) Assignees: Denso Corporation, Kariya (JP); Nippon Soken, Inc., Nishio (JP); Toyota Jidosha Kabushiki Kaisha, Toyota (JP)

( * ) Notice: Subject to any disclaimer, the term of this patent is extended or adjusted under 35 U.S.C. 154(b) by 300 days.

(21) Appl. No.: 12/122,301

(22) Filed: May 16, 2008

(65) Prior Publication Data

US 2008/0282779 A1    Nov. 20, 2008

(30) Foreign Application Priority Data

May 17, 2007    (JP)    ............................. 2007-132076

(51) Int. Cl.
*G01N 33/28*    (2006.01)
(52) U.S. Cl. ........................................................ 356/70
(58) Field of Classification Search .................... 356/70
See application file for complete search history.

(56) References Cited

FOREIGN PATENT DOCUMENTS

| JP | 61-113055 | 7/1986 |
|----|-----------|--------|
| JP | 5-133886  | 5/1993 |
| JP | 5-287597  | 11/1993 |

*Primary Examiner*—Gregory J Toatley, Jr.
*Assistant Examiner*—Amanda H Merlino
(74) *Attorney, Agent, or Firm*—Nixon & Vanderhye PC

(57) ABSTRACT

A fuel property sensor is provided with three bypass passages and a measure passage. The measure passage is located inside of a closed loop which is comprised of common tangential lines of adjacent bypass passages and a part of profile line of each bypass passage in a cross section perpendicular to the measure passage. Even if the fuel property sensor is rotated around the axis of a fuel pipe in assembling the fuel property sensor to the fuel pipe, at least one of two bypass passages is always located above the measure passage in a vertical direction. Hence, bubbles included in the fuel are restricted from flowing into the measure passage. The fuel property sensor can detect the concentration of ethanol contained in the fuel with high accuracy.

6 Claims, 3 Drawing Sheets

FUEL PROPERTY DETECTOR

CROSS-REFERENCE TO RELATED APPLICATION

This application is based on Japanese Patent Application No. 2007-132076 filed on May 17, 2007, the disclosure of which is incorporated herein by reference.

FIELD OF THE INVENTION

The present invention relates to a fuel property detector which detects fuel property. The light is emitted toward the fuel and transmitted therethrough. The fuel property detector detects the fuel property based on the transmitted light intensity.

BACKGROUND OF THE INVENTION

In a conventional fuel property detector shown in JP-5-133886A, a light-emitting diode (LED) emits light to fuel and a photodiode receives the light transmitted the fuel. Based on the transmitted light intensity, the detector detects concentration of ethanol contained in the fuel such as gasoline. Receiving the heat, temperature of the fuel may be increased and pressure in the fuel may fluctuate. Thereby, bubbles may arise in the fuel flowing in the fuel pipe. When the bubbles flows into the measure passage and adhere on at least one of a light emitting surface and a light receiving surface of the light-sensitive element, the light is refracted at the interface between the bubbles and the fuel. The intensity of the light entering the receiving surface of the light-sensitive element is fluctuated, so that an accuracy of fuel property detection may be deteriorated.

The present invention is made in view of the above matters, and it is an object of the present invention to provide a fuel property detector in which the fuel with bubbles is restricted from flowing into the measure passage, or the bubbles hardly adhere to the inner surface of the measure passage even if the fuel with bubbles flows into the measure passage. The fuel property is accurately detected according to the present invention.

According to the present invention, the fuel property detector is provided in a fuel pipe for detecting a property of fuel flowing through the fuel pipe. The fuel property sensor includes a housing having connecting ends which are connected to the fuel pipe, a measure passage which is defined in the housing and is opened at the connecting ends in order that the fuel flows therethrough, a light emitting element which is provided in the housing in such a manner as to emit a light toward the fuel in the measure passage, a light receiving element which is provided in the housing in such a manner as to receive the light passed through the measure passage, and a bypass passage which is defined in the housing in such a manner that the fuel flows therethrough. When the housing is connected to the fuel pipe, the bypass passage is located above the measure passage in a perpendicular direction in a cross section of the housing perpendicular to the measure passage. An inlet of the bypass passage is located above the inlet of the measure passage.

Receiving the heat, temperature of the fuel may be increased and pressure in the fuel may fluctuate, so that bubbles may arise in the fuel flowing in the fuel pipe. Since specific gravity of bubbles is lower than that of the fuel, the bubbles flows in an upper region in the fuel pipe. The fuel with bubbles flows into the bypass passage and the fuel without bubbles flows into the measure passage. Hence, the bubbles hardly adhere on a surface of the measure passage. Especially, the bubbles hardly adhere an emitting surface of light emitting element and a receiving surface of light receiving element. It is prevented from deteriorating an accuracy of fuel property detection may be deteriorated. The fuel property sensor can detect the fuel property with high accuracy.

BRIEF DESCRIPTION OF THE DRAWINGS

Other objects, features and advantages of the present invention will become more apparent from the following description made with reference to the accompanying drawings, in which like parts are designated by like reference numbers and in which.

DETAILED DESCRIPTION OF EMBODIMENTS

Referring to drawings, embodiments of the present invention, which is applied to a fuel property sensor 1 mounted on a vehicle, will be described hereinafter.

First Embodiment

Figure 3:
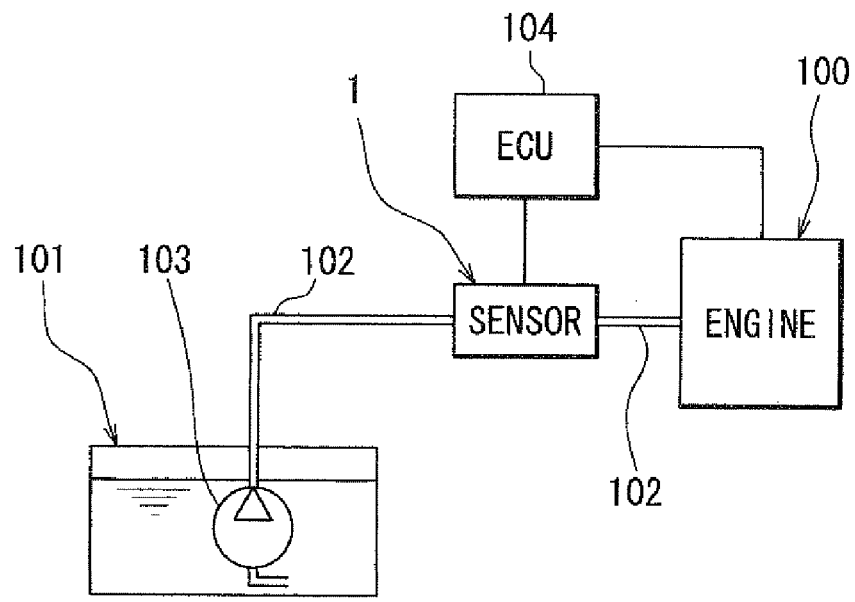
FIG. 3 is a schematic view showing a fuel circuit of an engine to which the fuel property sensor is provided.

As shown in FIG. 3, a fuel property sensor 1 is provided in a fuel pipe 102. Fuel in a fuel tank 101 is pumped up by a fuel pump 103 and supplied to an engine 100 through the fuel pipe 102. The fuel property sensor 1 is electrically connected to an electronic control unit (ECU) 104 which performs fuel injection control. The ECU 104 includes a microcomputer and the like.

The fuel supplied to the engine 100 will be described. The fuel supplied to the engine 100 is a mixture of gasoline and ethanol. The engine 100 can be operative by gasoline of 100%, ethanol of 100%, or mixture of gasoline and ethanol at any mixture rate. The fuel property sensor 1 detects ethanol concentration in the mixture. The ethanol concentration is one of fuel property. The ECU 104 controls fuel injection quantity, fuel injection timing, and the like based on the ethanol concentration to obtain desirable engine torque and to reduce emission.

A structure of the fuel property sensor 1 will be described hereinafter.

Figure 2:
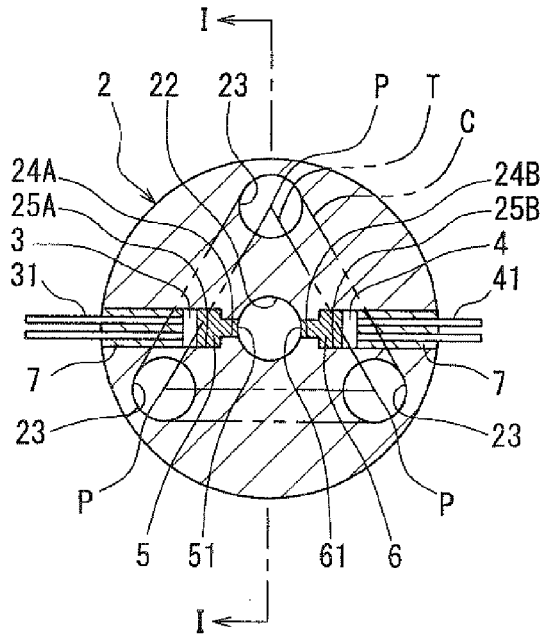
FIG. 2 is a cross sectional view taken along a line II-II in FIG. 1.

The fuel property sensor 1 includes a housing 2 which has connecting ends 21 connected to the fuel pipe 102. The housing 2 is provided with a measure passage 22 through which the fuel flows. As shown in FIG. 2, the fuel property sensor 1 includes a light-emitting diode (LED) 3, a phototransistor 4, and bypass passages 23. The LED 3 is provided in the housing 2 in such a manner as to emit light toward the measure passage 22. The phototransistor is provided in the housing 2 in such a manner as to receive the light emitted from the LED 3 through the fuel in the measure passage 22. The bypass passages 23 are opened at the connecting ends 21 of the housing 2, so that the fuel flows therethrough.

The housing 2 is made of metal material or resin material. In a case that the housing 2 is made of resin material, the resin material has heat-resistant against an environment temperature at a fixing portion of the sensor 1 and a maximum temperature of the fuel. The resin material also has light blocking effect. FIG. 2 is a cross sectional view taken along a line II-II in FIG. 1. As shown in FIG. 2, the measure passage 22 has a circular cross section. During engine operation, the fuel flows in the fuel pipe 102 and the measure passage 22 as indicated by arrows in FIG. 1. The housing 2 includes three bypass passages 23. The cross section of the bypass passages 23 are circle of which diameter is the same as each other. Longitudinal axes of the bypass passages 23 and the measure passage 22 are parallel to each other. As shown in FIG. 2, the measure passage 22 is located inside of a closed loop C which is comprised of common tangential lines of adjacent bypass passages 23 and a part of profile line of each bypass passage 23. Further, the measure passage 22 is located inside of an equilateral triangle T which connects center point P of each bypass passage 23. The fuel property sensor 1 in this embodiment can detects the ethanol concentration even when the fuel flows in reverse direction relative to the arrows in FIG. 1.

The housing 2 is provided with holes 24A and 24B which are on the same axis passing through the measure passage 22. The hole 24A and the hole 24B are opposed to each other. Further, the housing 2 is provided with large holes 25A and 25B which are on the same axis as the holes 24A and 24B. The hole 24A and the large hole 25A receive a window member 5, and the hole 24B and the large hole 25B receive a window member 6. The window members 5 and 6 are made of transparent material, such as resin material and glass material.

The LED 3 is arranged in the large hole 25A in such a manner that a light emitting surface of the LED 3 is in contact with the window member 5. Lead wires 31 of the LED 3 extend outside of the large hole 25A. The large hole 25A is filled with resin material 7 to hold the LED 3 air-tightly and the lead wires 31 with electrical insulation. The phototransistor 4 is arranged in the large hole 25B in such a manner that a light receiving surface of the phototransistor 4 is in contact with the window member 6. Lead wires 41 of the phototransistor 4 extend outside of the large hole 25B. The large hole 25B is filled with resin material 7 to hold the phototransistor 4 air-tightly and the lead wires 41 with electrical insulation. The lead wires 31, 41 are connected to an electric circuit through connectors (not shown).

The housing 2 is provided with flanges 26 at the connecting ends 21. The fuel pipe 102 also has flanges 102a. The flanges 26 and the flanges 102a are respectively connected, so that the fuel property sensor 1 is fixed in the fuel pipe 102.

An operation of the fuel property sensor 1 according to the first embodiment will be described.

The LED 3 is controlled to emit the light in a constant intensity. The light emitted from the LED 3 enters the window member 5 and emerges from an emitting surface 51 of the window member 5 into the measure passage 22. The light passed through the fuel in the measure passage 22 enters a receiving surface 61 of the window member 6 and reaches the phototransistor 4. The phototransistor 4 outputs signals according to the intensity of received light. Since the LED 3 is controlled to emit the light in a constant intensity, the intensity of the light in the measure passage 22 is always constant. The intensity of light that the phototransistor 4 receives is varied according to the ethanol concentration. Hence, the ethanol concentration can be detected based on the signal from the phototransistor 4.

Functions and advantages of the bypass passages 23 will be described.

Figure 1:
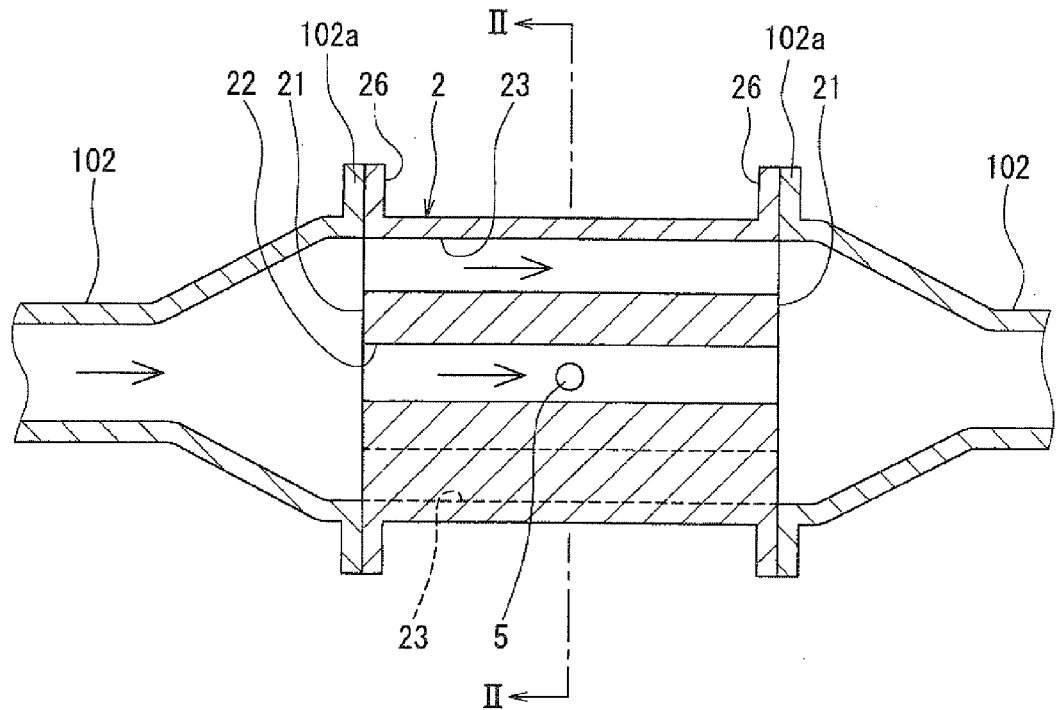
FIG. 1 is a longitudinal sectional view of a fuel property sensor according to a first embodiment.

According to the first embodiment, the fuel property sensor 1 is horizontally mounted. That is, the axial direction of the fuel pipe 102 and the measure passage 22 are horizontally arranged. The upper potion of the fuel property sensor 1 in FIGS. 1 and 2 is actually positioned in upper portion.

When the fuel in the fuel tank 101 is pumped up by the fuel pump 103, a motor (not shown) of the fuel pump 103 generates heat. Receiving the heat, temperature of the fuel is increased and pressure in the fuel fluctuates. Thereby, bubbles may arise in the fuel flowing in the fuel pipe 102. When the bubbles flows into the measure passage 22 and adheres on at least one of the emitting surface 51 and the receiving surface 61, the light is refracted at the interface between the bubbles and the fuel. The intensity of the light entering the receiving surface 61 is fluctuated, so that an accuracy of fuel property detection may be deteriorated.

As described above, the fuel property sensor 1 is provided with three bypass passages 23. The measure passage 22 is located inside of the closed loop C and the equilateral triangle T.

Even if the fuel property sensor 1 is rotated around the axis of the fuel pipe 102 in assembling the fuel property sensor 1 to the fuel pipe 102, at least one of three bypass passages is always located above the measure passage 22 in a vertical direction.

The bubbles in the fuel flow upper portion in the fuel pipe 102. When the fuel with bubbles reaches the fuel property sensor 1, the bubbles flow into the bypass passage 22 located above the measure passage 22. The fuel without bubbles flows into the measure passage 22. The bubbles are restricted from flowing into the measure passage 22. Hence, the fuel property sensor 1 can detect the concentration with high accuracy.

Second Embodiment

Figure 4:
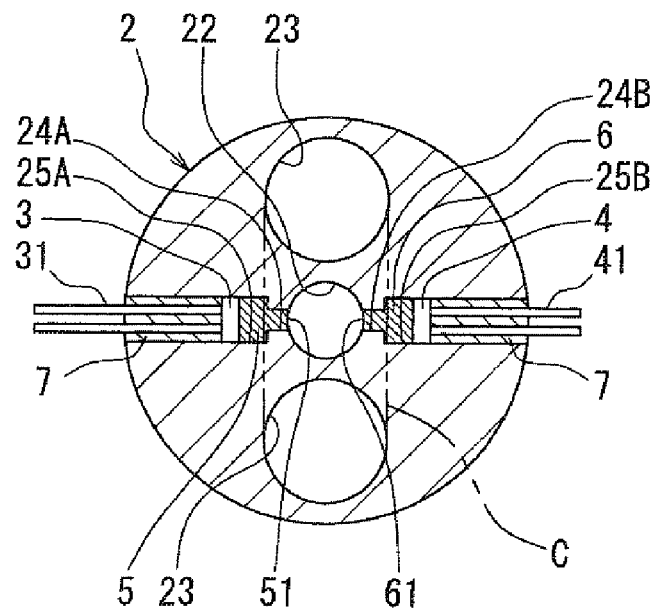
FIG. 4 is a cross sectional view of a fuel property sensor according to a second embodiment.

FIG. 4 is a cross sectional view of a fuel property sensor 1 according to a second embodiment. The fuel property sensor 1 includes two bypass passages 23.

The shape of cross section of the measure passage 22 and the shape of cross section of the bypass passages 23 are circle. The diameter of the bypass passages 23 is larger than that of the measure passage 22. The measure passage 22 is located inside of a closed loop C which is comprised of common tangential lines of adjacent bypass passages 23 and a part of profile line of each bypass passage 23. Even if the fuel property sensor 1 is rotated around the axis of the fuel pipe 102 in assembling the fuel property sensor 1 to the fuel pipe 102, at least one of two bypass passages is always located above the measure passage 22 in a vertical direction. Hence, the bubbles are restricted from flowing into the measure passage 22. The fuel property sensor 1 can detect the concentration with high accuracy.

Third Embodiment

Figure 5:
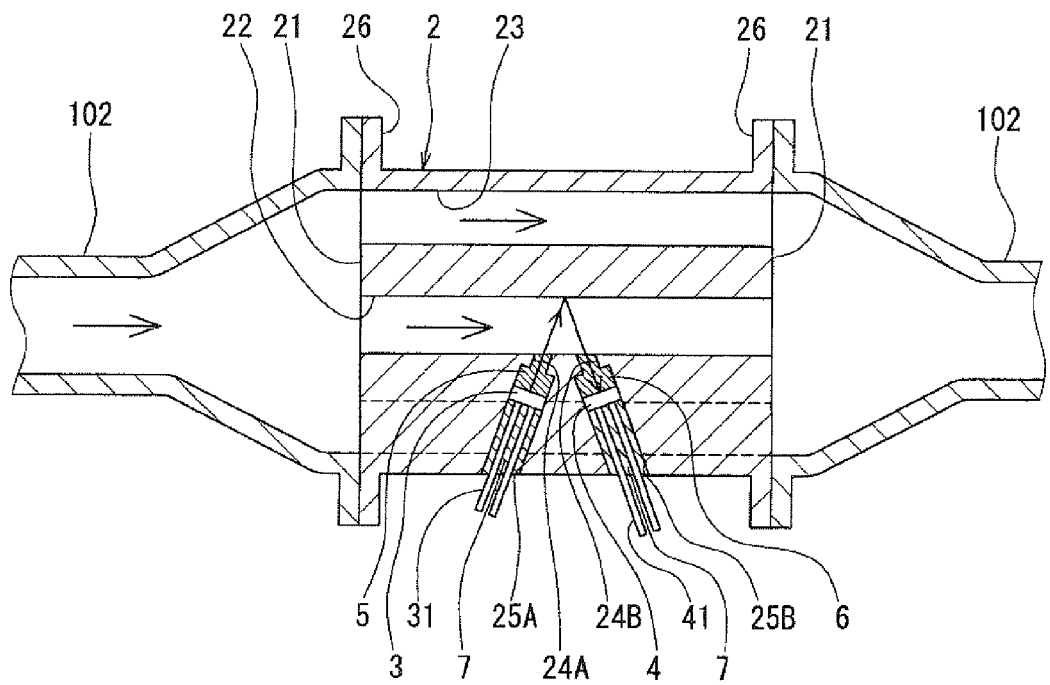
FIG. 5 is a longitudinal sectional view of a fuel property sensor according to a third embodiment.

Referring to FIG. 5, a third embodiment will be described.

The positions of the LED 3 and the phototransistor 4 relative to the measure passage 22 in the third embodiment are different from the first embodiment. The other structure of the fuel property sensor 1 is the same as the first embodiment.

According to the third embodiment, the LED 3 and the phototransistor 4 are located at the same angle position in a circumpherentially direction of the measure passage 22. As shown in FIG. 5, the holes 24A, 24B, and the large holes 25A, 25B are located at the same angle position in the circumpherentially direction of the measure passage 22. The hole 24A and the large hole 25A receive a window member 5. The LED 3 is arranged in the large hole 25A in such a manner that a light emitting surface of the LED 3 is in contact with the window member 5. The Lead wires 31 of the LED 3 extend outside of the large hole 25A. The large hole 25A is filled with resin material 7 to hold the LED 3 air-tightly and the lead wires 31 with electrical insulation. The hole 24B and the large hole 25B receive a window member 6. The phototransistor 4 is arranged in the large hole 25B in such a manner that a light receiving surface of the phototransistor 4 is in contact with the window member 6. The lead wires 41 of the phototransistor 4 extend outside of the large hole 25B. The large hole 25B is filled with resin material 7 to hold the phototransistor 4 air-tightly and the lead wires 41 with electrical insulation.

The light emitted from the LED 3 enters the window member 5 and emerges from an emitting surface 51 of the window member 5 into the measure passage 22. The light passed through the fuel in the measure passage 22 is refracted at an inner surface of the measure passage 22. The refracted light enters the receiving surface 61 of the window member 6 and reaches the phototransistor 4. The phototransistor 4 outputs signals according to the intensity of received light.

When the fuel with bubbles reaches the fuel property sensor 1, the bubbles flow into the bypass passage 22 located above the measure passage 22. The fuel without bubbles flows into the measure passage 22. The bubbles are restricted from flowing into the measure passage 22. Hence, the fuel property sensor 1 can detect the concentration with high accuracy.

According to the third embodiment, since the light is reflected at the inner wall of the measure passage 22, a light path from the emitting surface 51 to the receiving surface 61 is elongated. A ratio of the light path in the fuel relative to the whole light path from the LED 3 to the phototransistor 4 is enlarged, so that the accuracy of the fuel property detection is enhanced.

Furthermore, according to the third embodiment, since the LED 3 and the phototransistor 4 are located at the same angle in the circumpherentially direction of the measure passage 22, the lead wire 31 and the lead wire 41 are extended in the same angle. The connectors connecting the LED 3 and the phototransistor 4 to the ECU 104 can be arranged at almost the same position.

The inner surface of the measure passage 22 may be polished, plated, or coated to enhance the reflecting ratio thereof.

Fourth Embodiment

Figure 6:
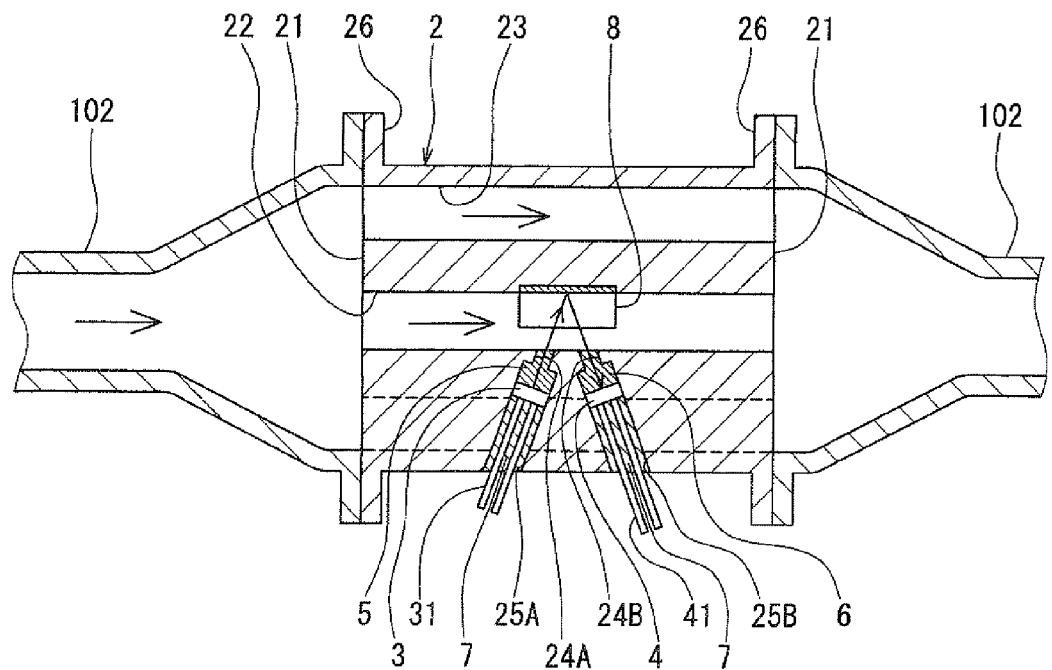
FIG. 6 is a longitudinal sectional view of a fuel property sensor according to a fourth embodiment.

Referring to FIG. 6, a fourth embodiment will be described.

The fuel property sensor 1 has a reflecting plate 8 in the measure passage 22. The light emitted from the LED 3 is reflected at the reflecting plate 8 toward the phototransistor 4. The structure of the reflecting plate 8 will be described hereinafter. The other structure is the same as the third embodiment.

The reflecting plate 8 is made of resin material or metal material and has a mirror-finished surface confronting the LED 3 and the phototransistor 4. The reflecting plate 8 is arc-shaped along the inner surface of the measure passage 22. The reflecting plate 8 is located in the measure passage 22 in such a manner as to surely receive the light emitted by the LED 3. The reflecting plate 8 is fixed by welding or press-insertion. Alternatively, when the housing 2 is formed by molding metallic material or resin material, the reflecting plate 8 may be fixed in the housing 2 by insert molding.

The reflecting plate 8 increases the light entering the phototransistor 4 to enhance the accuracy of the fuel property detection.

The shapes of cross section of the measure passage 22 and the bypass passage 23 are not limited to a circle.

More than three bypass passages 23 can be provided around the measure passage 22 in such a manner as the first embodiment in order that the bubbles is restricted from flowing into the measure passage 22.

In the above embodiments, a photodiode can be used instead of the phototransistor 4.

The measure passage 22 may be formed by fuel-attracting material. For example, the housing 2 is made of resin material and a pipe made of tile is provided in the housing 2 to form the measure passage 22 therein. Generally, in a case that the inner surface of the pipe is not fuel attracting, the bubbles in the fuel easily adhere to the inner surface. In a case that the inner surface of the pipe is fuel attracting, the bubbles in the fuel hardly adhere to the inner surface of the pipe. Hence, when the measure passage 22 is made of fuel-attracting material, the bubbles hardly adhere to the inner surface of the measure passage 22. Even if the fuel with bubbles flows into the measure passage 22, the bubbles hardly adhere to the inner surface of the measure passage 22 so that the accuracy of the fuel property detection is not deteriorated.

The present invention can be applied to other than the fuel property sensor. For example, the present invention can be applied for detecting concentration of components in lubricant oil or operation fluid of an automatic transmission. The present invention can be applied to other than for automobiles. For example, the present invention can be used for detecting concentration of particles in fuel of a combustion-type heater.

What is claimed is:

1. A fuel property detector provided in a fuel pipe for detecting a property of fuel flowing through the fuel pipe, comprising:
    a housing having connecting ends which are connected to the fuel pipe;
    a measure passage which is defined in the housing and is opened at the connecting ends in order that the fuel flows therethrough;
    a light emitting element which is provided in the housing in such a manner as to emit a light toward the fuel in the measure passage,
    a light receiving element which is provided in the housing in such a manner as to receive the light passed through the measure passage; and
    a bypass passage which is defined in the housing in such a manner that the fuel flows therethrough, wherein
    when the housing is connected to the fuel pipe, the bypass passage is located above the measure passage in a perpendicular direction in a cross section of the housing perpendicular to the measure passage.

2. A fuel property detector according to claim 1, wherein a plurality of bypass passages are defined in the housing.

3. A fuel property detector according to claim 2, wherein the measure passage is located inside of a closed loop which is comprised of common tangential lines of adjacent bypass passages and a part of profile line of each bypass passage in a cross section of the housing perpendicular to the measure passage.

4. A fuel property detector according to claim 1, wherein three or more bypass passages are provided, and
the measure passage is located inside of a polygon which connects center points of each bypass passage in a cross section of the housing perpendicular to the measure passage.

5. A fuel property detector according to claim 1, further comprising a reflecting member arranged in the measure passage in such a manner as to reflect the light to the light-receiving element.

6. A fuel property detector according to claim 1, wherein the measure passage is defined by a wall on which fuel-attracting treatment is provided.

* * * * *